United States Patent
Shug et al.

(10) Patent No.: US 7,655,259 B2
(45) Date of Patent: Feb. 2, 2010

(54) DELAYED RELEASE CARNITINE

(75) Inventors: Austin L. Shug, Madison, WI (US); Carl E. Gulbrandsen, Madison, WI (US)

(73) Assignee: SIGMA-TAU Industrie Farmaceutiche Riunite S.p.A, Rome (IT)

( * ) Notice: Subject to any disclaimer, the term of this patent is extended or adjusted under 35 U.S.C. 154(b) by 44 days.

(21) Appl. No.: 11/670,671

(22) Filed: Feb. 2, 2007

(65) Prior Publication Data

US 2007/0160669 A1    Jul. 12, 2007

Related U.S. Application Data

(63) Continuation of application No. 11/223,086, filed on Sep. 9, 2005, now abandoned, which is a continuation of application No. 10/384,085, filed on Mar. 7, 2003, now abandoned, which is a continuation of application No. 08/109,159, filed on Aug. 19, 1993, now abandoned, which is a continuation-in-part of application No. 08/078,985, filed on Jun. 16, 1993, now abandoned.

(51) Int. Cl.
*A61K 9/16* (2006.01)
*A61K 9/14* (2006.01)
*A61K 9/48* (2006.01)
*A61K 9/52* (2006.01)
*A61K 9/20* (2006.01)
*A61K 9/22* (2006.01)

(52) U.S. Cl. ............... 424/490; 424/451; 424/457; 424/464; 424/468; 424/489; 424/497

(58) Field of Classification Search ............ 424/400, 424/464, 468, 489
See application file for complete search history.

(56) References Cited

U.S. PATENT DOCUMENTS

| 3,810,994 A | * | 5/1974 | Wiegand |
| 4,681,755 A | * | 7/1987 | Colombo et al. |
| 4,871,550 A | * | 10/1989 | Millman ............ 424/601 |
| 5,178,878 A | * | 1/1993 | Wehling et al. |

* cited by examiner

*Primary Examiner*—Humera N Sheikh
(74) *Attorney, Agent, or Firm*—Lucas & Mercanti, LLP

(57) ABSTRACT

A sustained release, orally administered pharmaceutical composition comprising carnitine and an acceptable pharmaceutical excipient is described for the treatment of carnitine deficiency and other carnitine responsive conditions. The sustained release formulation avoids the characteristic problems of gastrointestinal invitation, dumping in the urine and bacterial degradation attendant previously known oral formulations of carnitine.

3 Claims, 3 Drawing Sheets

L-Carnitine Release vs. Time

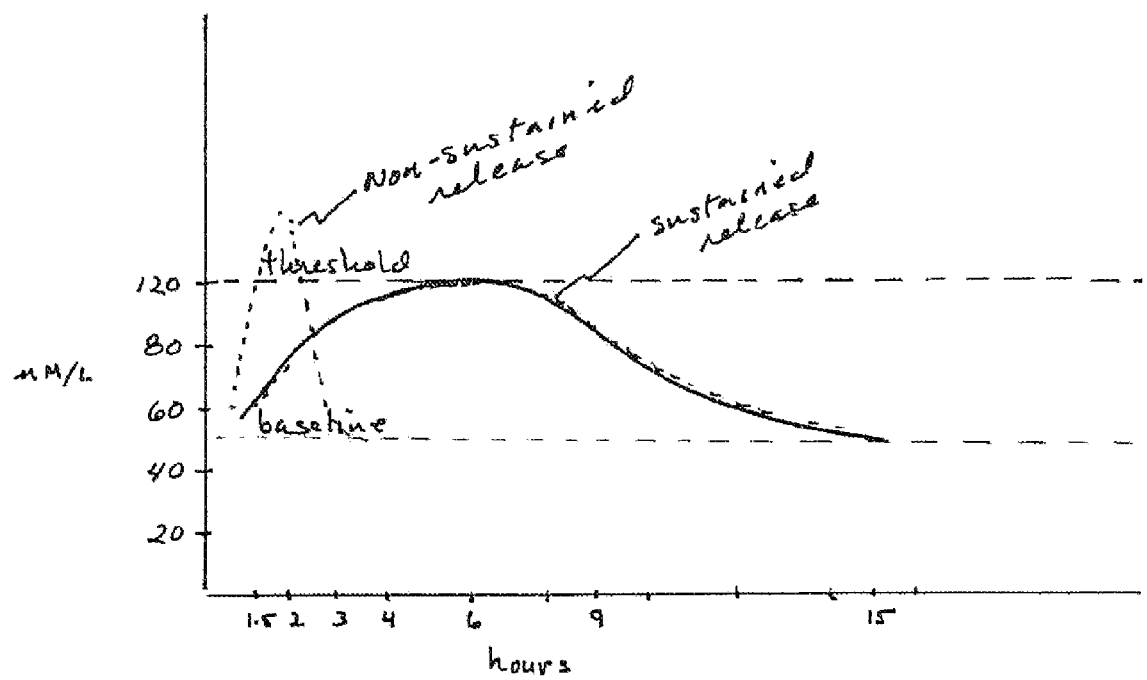

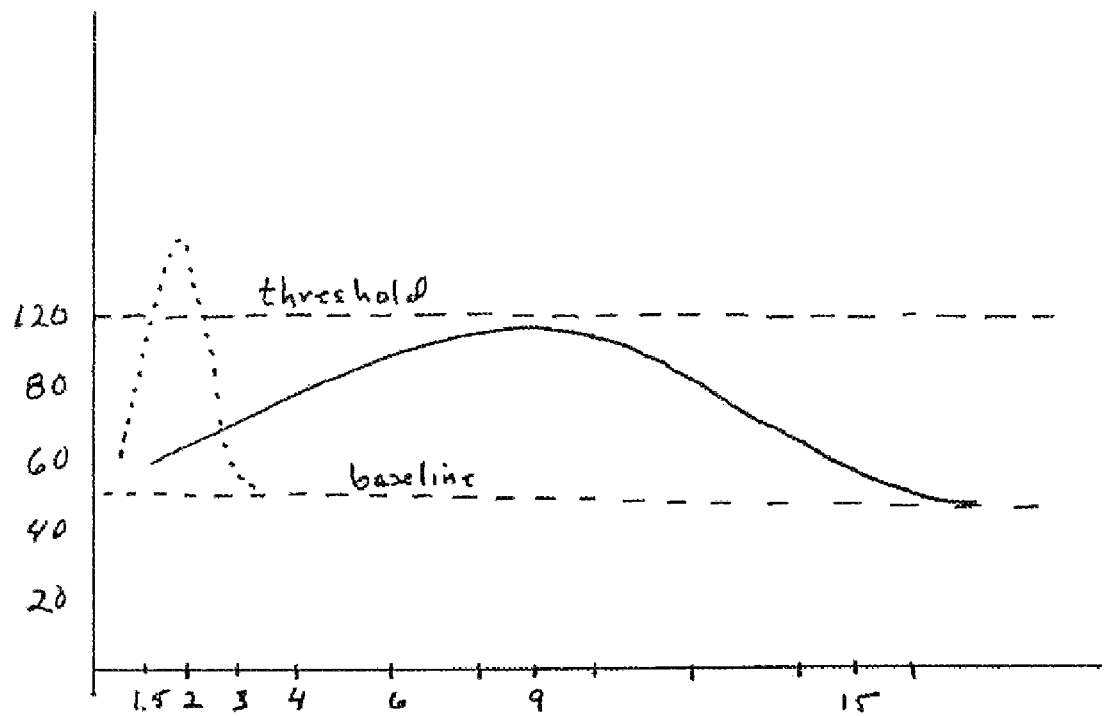

DELAYED RELEASE CARNITINE

CROSS REFERENCE TO RELATED APPLICATIONS

This application is a continuation of U.S. Ser. No. 11/223,086, filed Sep. 9, 2005, now abandoned which, in turn is a continuation of U.S. Ser. No. 10/384,085, filed on Mar. 7, 2003, now abandoned, which, in turn, is a continuation of U.S. patent application Ser. No. 08/109,159, filed on Aug. 19, 1993, now abandoned, which in turn is a continuation-in-part of U.S. patent application Ser. No. 08/078,985, filed on Jun. 16, 1993, now abandoned, the contents of each of which are incorporated herein by reference.

TECHNICAL FIELD

The invention relates to the field of sustained release pharmaceutical preparations and more specifically to a sustained release pharmaceutical preparation containing L-carnitine or gamma butyrobetaine.

BACKGROUND OF THE INVENTION

L-carnitine 3-hydroxy-4-(trimethylamino-)butyrate is a naturally occurring quaternary amine that is required in energy metabolism in mammals. The L-carnitine molecule has been shown to promote oxidation of branched-chain amino acids, the utilization of acetyl-coenzyme A, and the removal of extra or "toxic" acyl groups from the mitochondria and cell as carnitine esters. Arguably its most important function, however, is the promotion of beta-oxidation of long chain fatty acids by facilitating their transfer across the mitochondrial membrane.

Because of its central role in transporting fatty acids to the site of oxidation, adequate levels of L-carnitine are required for normal fatty acid and energy metabolism in those tissues, such as the heart, which preferentially metabolize fatty acids. In the human, L-carnitine is synthesized endogenously from the amino acids, lysine and methionine. Meat products, particularly red meats (beef, lamb and pork) and dairy products are important dietary sources of L-carnitine. None-the-less, carnitine deficiency can occur in humans ad presents a characteristic syndrome. Affected individuals may display mild to severe muscle weakness, hypoglycemia, liver dysfunction and cardiomyopathy. It detected early, the syndrome is often completely reversible with daily administration of adequate amounts of L-carnitine.

Gamma-butyrobetaine ("GBB") is the immediate precursor to L-carnitine in the biosynthetic pathway of the latter compound. It is disclosed in U.S. Pat. No. 4,382,092, incorporated herein by reference, that GBB given orally will be readily converted to L-carnitine in carnitine deficient patients and is thus a suitable substitute for L-carnitine in treating such deficiencies. GBB has the advantage of being much less expensive to chemically synthesize than is L-carnitine. Hereafter, the term "carnitine" will be understood to refer to either L-carnitine or GBB, as well as their biologically active salts and esters, but not D-carnitine, the latter compound being hereby specifically excluded.

Some forms of organic aciduria have been treated with L-carnitine administration. In some such cases the affected individual must be given as much as 400 mg/k/day of L-carnitine.

Carnitine is also considered by some authorities to be a useful and important nutritional supplement, particularly for older persons who frequently show elevated esterified carnitine levels in the serum. Some evidence exists that carnitine supplementation enhances the immune system, muscle efficiency, and overall well being of the person using carnitine supplementation.

More recently, it has been found that carnitine is useful in patients suffering from or predisposed to osteoporosis. In such individuals it is believed that daily administration of carnitine will reduce the loss of bone mass. Co-pending U.S. application Ser. No. 07/907,847, incorporated herein by reference, discloses that daily administration of carnitine in amounts from 50 to 200 mg/kilogram will result in a significantly reduced loss of bone mass.

Oral formulations of L-carnitine are available in tablet or capsule form. The inventors are not aware of any commercially available oral dosage formulation of GBB. None of the heretofore known oral formulations of L-carnitine provide a sustained release of L-carnitine. Common dosage forms of the presently available oral formulations are usually 250 to 500 mg per tablet or capsule. Principal suppliers of pharmaceutical grade L-carnitine are Sigma Tau SpA, Rome, Italy; Aginomoto, Terrance, Calif.; and Lanza Chemical Company, Berne, Switzerland.

Where L-carnitine is being administered to treat carnitine deficiency dosages as high as 400 mg/K/day may have to be given. The customary dosage amount for mild to moderate carnitine deficiency is 50 to 100 mg/k/day.

Because the half-life of L-carnitine in the human is approximately 30 minutes, the usual dosage regimen is to administer an excess amount of L-carnitine four times each day. If the dosage formulation is 250 mg/tablet, one would expect a 70 kilogram mildly deficient individual to take 7 tablets, four times each day (or 28 tablets/day) in order to restore L-carnitine to normal plasma levels.

A number of disadvantages exist with the presently available dosage forms of L-carnitine. First, the renal threshold for L-carnitine is about 80 to 120 microM/L. This threshold is invariably exceeded when large amounts of L-carnitine are given and thus much of the otherwise useful L-carnitine is "dumped" in the urine. Second, L-carnitine is subject to breakdown by the bacteria of the gut and when large boluses of the drug are given, a fair amount is lost through bacterial breakdown. Third, L-carnitine can cause gastrointestinal irritation resulting in gastrointestinal distress and diarrhea. Such problems are exacerbated when frequency of administration and dosage levels are both high.

The present invention avoids most, if not all, of the above stated disadvantages. Additionally, it allows for a much more convenient dosage regimen (e.g., once or twice per day) with greater efficacy than its nonsustained release counterpart.

SUMMARY OF THE INVENTION

The present invention provides an oral formulation of carnitine which virtually eliminates the above recited problems of dumping of carnitine in the urine, bacterial breakdown of carnitine by intestinal bacteria, and gastrointestinal distress and diarrhea when daily administration of large amounts of L-carnitine are recommended. Using the invention, methods of treating various carnitine responsive disorders are disclosed.

Accordingly, it is an object of this invention to provide a sustained release carnitine drug preparation useful in the treatment or prevention of L-carnitine deficiency or other L-carnitine responsive disorders, such as osteoporosis, which does not cause adverse GI symptoms, such as gastrointestinal distress and diarrhea.

It is a specific object of this invention to provide a sustained release, unitary dosage, oral formulation of carnitine which upon administration releases carnitine at a slow rate over the course of at least several hours, preferably a maximum of eight hours without causing the gastrointestinal irritation.

It is another object of the invention to provide a method for treating or preventing L-carnitine deficiency by administering, at least once daily, to a patient suffering from or at risk for L-carnitine deficiency, a sustained release, unitary dosage product containing sufficient amount of carnitine effective to increase the serum L-carnitine to normal level.

It is a further object of the invention, to provide a method for treating or preventing carnitine responsive, age-related disorders, such as osteoporosis, by administering, at least once daily, to a patient suffering from or predisposed to said carnitine responsive, age-related disorder a sustained release, unitary dosage formulation of carnitine (alone or in combination with one or more other active ingredients) effective for the maintenance of or formation and strengthening of diseased or weakened tissues such as muscle and bone.

In accordance with these objectives and other objects, which will become apparent from the following description, the present invention provides, in one aspect thereof, a medication for providing carnitine for the treatment or prevention of L-carnitine deficiency or osteoporosis, which is in the form of a unitary dosage formulation containing from about 100 milligrams (mg) to about 500 mg of carnitine. The formulation of the invention further includes a means for slowly releasing the aforesaid active ingredient(s) over a period of several to eight hours upon exposure to the gastrointestinal fluids. The formulation of the invention is designed to release carnitine at such a rate that the quantity of carnitine present in the stomach or intestine at any one time is below the amount likely to cause gastrointestinal irritation. The slowly released carnitine is readily absorbed and exposes less carnitine to bacterial degradation. The formulation of the invention is further designed so that the dosage of carnitine is slowly absorbed over period of several to eight hours. This controlled all sorption of carnitine over a period of hours limits the loss of carnitine due to dumping in the urine and thus makes more of the carnitine in the formulation available for use by the body.

The sustained release unitary dosage product of this invention may include L-carnitine or GBB as the sole active ingredient. Alternatively, L-carnitine or GBB may be used together in varying proportions, or one or the other may be used in combination with other active ingredients when used to treat other L-carnitine responsive age-related conditions such as osteoporosis. In the latter case, co-pending U.S. patent application Ser. No. 08/078,985, incorporated herein by reference, discloses the combination of L-carnitine or GBB and the hormone dehydroepiandrosterone or dehydroepiandrosterone-sulfate (hereafter referred to collectively as "DHEA") as a useful and desirable combination.

In a specific and preferred embodiment of the invention, the means for controlling release of carnitine and any other active ingredient includes a matrix of water swelling polymerization products. In the preferred embodiment, these products are acrylic and methacrylic acid esters having a low content of quaternary ammonium groups. The aforesaid polymerization products form a thin lacquer which completely coats small granules of the carnitine or GBB and other active ingredients if present. The polymer coating is water insoluble but slowly permeable. Upon introduction of the unitary dosage product into an aqueous medium, the polymeric coating swells and allows water to slowly permeate the preparation. Carnitine or GBB, both of which are highly water soluble, are dissolved in the slowly permeating water thereby slowly and uniformly released into the gastrointestinal tract.

According to the method aspect of the invention, a patient suffering from L-carnitine deficiency or from a carnitine responsive disorder such as osteoporosis is treated with at least one of the sustained release unitary dosage carnitine products of this invention.

DESCRIPTION OF THE DRAWINGS

FIG. 2 is a graph of total serum carnitine versus time.

FIG. 3 is a graph of total serum carnitine versus time.

DETAILED DESCRIPTION

Figure 1:
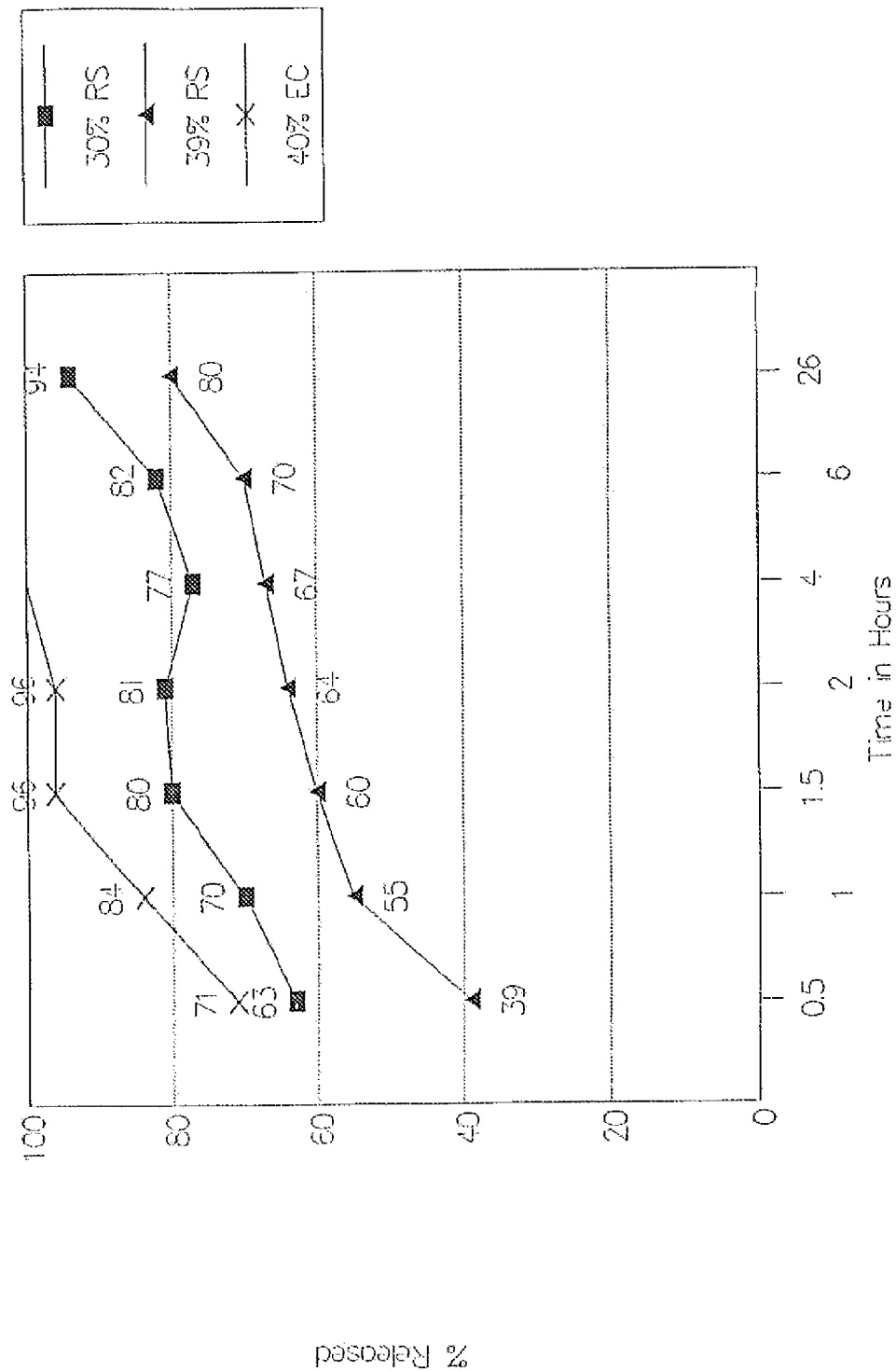
FIG. 1 is a graph of the percent carnitine released from coated carnitine versus time.

In accordance with the present invention, it has been found that by incorporating L-carnitine or GBB alone or in combination with one another in varying amounts, or in combination with another active ingredient, in a slow release dosage formulation, the occurrence of GI irritation associated with present administration practices can be completely avoided. Although not wishing to be bound by any particular theory, it is presumed that by only gradually releasing the carnitine from the unitary dosage product, the quantity of carnitine present in the stomach or intestine at any given time is below the threshold value at which gastrointestinal irritation will occur. By whatever means of action, by incorporating the carnitine with means for controlling the release of the carnitine over a period extending up to a maximum of eight hours from the time of ingestion, gastrointestinal irritation will be avoided.

The invention also permits more of the carnitine to be made available for use by the body than was heretofore possible with previously available oral dosage formulations of carnitine. This is because the present invention reduces the amount of carnitine lost through bacterial degradation and dumping in the urine. Again, without being bound by any particular theory, it is believed that by providing a slow release of carnitine in the gastrointestinal tract, the carnitine released at any one time is rapidly absorbed into the blood stream. Thus, the carnitine is not exposed to the intestinal bacterial for any significant period of time unlike heretofore oral dosage formulations of carnitine. The very limited exposure to intestinal bacteria greatly reduces the proportion of carnitine degraded by bacterial action. Additionally, by allowing for absorption of carnitine into the blood stream over a period of hours rather than minutes, the increase in plasma carnitine is gradual and sustained. Under such circumstances, the renal threshold is only modestly exceeded, if at all, and less of the carnitine is dumped in the urine. As a consequence of both the decrease in bacterial degradation and urine dumping more of the administered carnitine is available for use by the body.

The present invention surprisingly results in greater carnitine tissue concentrations than was heretofore possible with previously available oral dosage formulations of carnitine. It is known that tissue carnitine levels are dependent on plasma carnitine levels. Thus chronically low plasma carnitine will ultimately result in all body tissues having lower carnitine levels. Restoration toward normal of carnitine tissue concentrations in a chronically carnitine deficient individual has heretofore been only moderately successful with oral dosing of carnitine for the reasons discussed above.

With the present invention, plasma carnitine levels are maintained at a higher level than was heretofore possible.

This results in a greater proportion of the administered carnitine being used to load the tissues thus serving to make the treatment more effective.

The means for providing controlled (i.e., sustained) release of the active ingredient may be selected from any of the known sustained-release delivery systems for controlling the release of an active ingredient over a course of about four or more hours including the wax matrix system, the miniature osmotic "pump" system and the Eudragit RL/RS system (of Rohm Pharma, GmbH, Weiterstadt, Germany).

The wax matrix system disperse the active ingredient(s) in a wax binder which slowly dissolves in body fluids to gradually release the active ingredient(s).

In the miniature osmotic "pump" an active ingredient is coated with a semipermeable membrane. The pump works when water-soluble drugs are released through a hole drilled in the membrane.

The preferred controlled-release oral drug delivery system is the Eudragit RL/RS system in which the active ingredient, L-carnitine or GBB, is formed into granules having a dimension of 25 to 30 mesh. The granules are then uniformly coated with a thin polymeric lacquer which is water insoluble but slowly water permeable. The coated granules are mixed with optional additives such as flavoring, binder, lubricant, processing aids and the like. The mixture is compacted into a tablet which, prior to use, is hard and dry. After the tablet is swallowed and comes into contact with the aqueous stomach and intestinal fluids, the thin lacquer begins to swell and slowly allows permeation of water. As water slowly permeates the lacquer coating, the active ingredients become dissolved in the water and are thereby slowly released. By the time the tablet has passed through the GI tract, after about four to eight hours, the active ingredients will have been slowly but completely released. Accordingly, the ingested tablet will release a stream of the L-carnitine or GBB as well as any other active ingredient.

The Eudragit system is comprised of high permeability lacquers (RL) and low permeability lacquers (RS). The permeability of the coating and thus the time course of drug release can be titrated by varying the proportion of RS to RL coating material.

For further details of the Eudragit RL/RS system, reference is made to technical publications available from Rohm Tech, Inc., 195 Canal Street, Maiden, Mass. 02146. See also, K. Lehmann, D. Dreher "Coating of tablets and small particles with acrylic resins by fluid bed technology," Int. J. Pharm. Tech. & Prod. Mfr. 2(r), 31-43 (1981).

The amount of the L-carnitine can generally be varied over a range of from about 250 mg to about 1.0 gm L-carnitine per tablet (or pill, capsule, etc.). Therefore, based on the current recommended dosage for treatment of carnitine deficiency of 50 mg/k/day to about 100 mg/k/day, total daily dosages of one or two tablets twice each day can provide the total recommended requirement of L-carnitine.

In the case of prevention or treatment of osteoporosis, the recommended daily dosage of L-carnitine, as per co-pending U.S. patent application Ser. No. 08/078,985 incorporated herein by reference, is approximately 2 gm/day. This dosage of carnitine is preferably given in combination with DHEA or DHEAS as disclosed in the aforementioned co-pending U.S. patent application Ser. No. 08/078,985. For purposes of the present invention the DHEA should be given will an amount of approximately 1.0 to 10 mg per day and more preferably in all approximate amount of 0.5 mg per day. Based on that recommendation, two tablets having a unit dosage of 500 mg carnitine and 0.175 mg DHEA given each ignoring and each evening of each day will provide the total recommended requirement of L-carnitine.

EXAMPLE 1

Sustained Release Formulation of Carnitine

A preferred formulation of a sustained-release unitary dosage tablet according to the invention which utilizes the Eudragit RL/RS system referred to above is shown immediately below: TABLE-US-00001 Ingredient Amount L-Carnitine 155.4 gm Eudragit RS100 72.7 gm L-carnitine was obtained in a fine powder foil from Metabolic Analysis Labs, Inc of Madison, Wis. The carnitine was wetted so as to form granules. The granules were screened through a 20 mesh screen. Eudragit RS100 was prepared as recommended by the manufacturer. The 20 mesh granules of carnitine were coated with the Eudragit coating using the Wurster™ process. This formulation provided a coating of about 39% by weight of very slowly water permeable lacquer. The coated carnitine was tested for sustained release by placing a known amount of the coated carnitine in a known volume of water. Samples of the water containing the coated carnitine were taken at 30 min., 60 min., 120 min., 240 min., and 360 min. The samples were analyzed for concentration of L-carnitine. Samples were also prepared using a 30% by-weight coating of Eudragit RS100 and a 40% by-weight coating of ethylene cellulose, another commonly used, sustained release coating. The graph of FIG. 1 shows the results of this study depicted as percent carnitine released v. time. As illustrated in the graph of FIG. 1, the L-carnitine having a 39% by-weight coating of RS100 prepared according to the present example gave a sustained release of L-carnitine over a period greater than six hours. The other two formulations gave too rapid a release of L-carnitine and are not preferred.

For administration to animals or humans, the coated material prepared in a manner described in Example 1, may be poured into a standard size gelatin capsule, or it may be compressed into a tablet form along with pharmaceutically acceptable filler material giving a final concentration per capsule (or tablet) of 500 mg carnitine/capsule. The final product is designed to release the L-carnitine in the gastrointestinal tract slowly over a period of up to eight hours after ingestion.

EXAMPLE 2

Pharmacokinetics Testing of Sustained Release L-Carnitine

A dog receives orally a capsule of sustained release L-carnitine formulated as described in this invention. Another dog receives a similar amount of the orally administered L-carnitine in a nonsustained release formulation. Blood is drawn at 0, 0.5, 1, 1.5, 2, 3, 4, 6, 9, and 15 hours after dose administration. The blood is analyzed for total plasma L-carnitine levels. The animal administered the drug in the sustained release formulation shows a slower rise in total plasma concentration of L-carnitine, a lower maximum concentration of total plasma L-carnitine and prolonged elevation of total plasma L-carnitine relative to the animal receiving the carnitine in a nonsustained release formulation. FIG. 2 depicts the total plasma levels of L-carnitine in μmoles per liter v. time expected from the above-described experiment.

EXAMPLE 3

Pharmacokinetics Testing of Sustained Release GBB

A study is done following the same protocol as that described in Example 2, above, except that GBB is orally administered in a sustained release form rather than L-carnitine. The study shows a slow rise in total plasma carnitine, a lower maximum concentration of L-carnitine and a prolonged elevation of total plasma L-carnitine relative to control. The pharmacokinetics of the sustained release GBB is similar to the sustained release L-carnitine, but as, shown in the graph of FIG. 3, the expected pharmacokinetic curve is shifted to the right. This study shows that GBB is a suitable substitute for L-carnitine.

EXAMPLE 4

Treatment of Carnitine Deficiency

A study is done with sustained release L-carnitine in carnitine deficient patients over the age of 60. The population is separated into a control group and an experimental group. The control group is administered one nonsustained release tablet containing 500 mg. each of L-carnitine, four times each day. The experimental group is administered sustained release tablets prepared according to the disclosure of Example 1, above, each tablet containing 500 mg of L-carnitine. The dosage regiment for the sustained release experimental group is two tablets twice daily, i.e., two tablets each morning at rising and two tablets each evening before bedtime. The study is continued for 20 weeks. Serum carnitine levels are checked in each patient at 0, 4, 8, 12, 16 and 20 weeks. The results of the study indicate that both the L-carnitine administered four times per day in the control group and the sustained release formulation administered twice each day, restore serum carnitine to a normal range. However, the control group shows a slight decrease in serum L-carnitine levels after eight weeks. The sustained release formulation consistently provides a slower rise in serum carnitine and a sustained higher average level of serum L-carnitine than does the nonsustained release tablet formulation. The study also shows that a significantly greater member of the control population experience gastrointestinal distress after taking L-carnitine than do the experimental population.

EXAMPLE 5

Treatment of Osteoporosis

A clinical study is conducted with postmenopausal osteoporotic outpatients having ages between 55 and 75 years. The study involves up to 120 patients randomly divided into three treatment groups, and continues for 24 months. Two of the treatment groups receive daily 2 grams of L-carnitine and 0.5 mg DHEAS. One of the treatment groups ("T1") receives the L-carnitine plus DHEAS in a nonsustained release dosage formulation containing 500 mg/tablet of L-carnitine and 0.175 mg DHEAS. The regiment for T1 is 1 tablet four times each day. The second treatment group ("T2") receives the L-carnitine in a sustained release formulation containing 500 mg/tablet of L-carnitine and 0.175 mg DHEAS. The regiment for T2 is 2 tablets twice a day, two upon rising in the morning and two before bedtime each evening. A third group receives a matching placebo; two tablets twice each day. All patients maintain a normal intake of dietary calcium (500 to 800 mg/day) and refrain from using calcium supplements. Efficacy is evaluated by pre- and post-treatment comparisons of the patient groups with regard to (a) total body, radial, femoral, and/or spinal bone mineral density as determined by x-ray absorptiometry (DEXA), and (b) determinations of serum osteocalcin. Safety is evaluated by comparisons of urinary hydroxyproline excretion, serum and urine calcium levels, creatinine clearance, blood urea. nitrogen, and other routine determinations and patient complaints related to gastrointestinal disturbances.

This study is expected to demonstrate that T2 patients treated with orally administered sustained release formulation L-carnitine and DHEAS exhibit significantly higher total body, radial, femoral, and/or spinal bone densities relative to the T1 patients treated with nonsustained release dosage form or placebo. The T2 treated patients also exhibit significant elevations in serum osteocalcin relative to the other groups. The monitored safety parameters confirm an insignificant incidence of gastrointestinal irritation for the T2 treatment group and the placebo. A significant proportion of the T1 treatment group, however, complain of gastrointestinal irritation.

EXAMPLE 6

Prevention of Osteoporosis

A clinical study is conducted with healthy postmenopausal women having ages between 55 and 60 years. The study involves up to 80 patients randomly divided into two treatment groups, and continues for 12 to 24 months. One treatment group receives sustained release formulation L-carnitine and DHEAS (twice each day; dosage: 2 mg L-carnitine and 0.5 mg DHEAS each day) and the other receives a matching placebo. The study is conducted as indicated in Example 5 above.

This study demonstrates that patients treated with sustained release formulation L-carnitine exhibit reduced losses in total body, radial, femoral, and/or spinal boric densities relative to baseline values. In contrast, patients treated with placebo show significant losses in these parameters relative to baseline values. The monitored safety parameters confirm that none of the treatment groups experienced gastrointestinal irritation as a-result of taking the sustained release formulation L-carnitine.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest claims.

The invention claimed is:

1. A method of reducing gastrointestinal irritation associated with carnitine therapy in humans, comprising administering a sustained release formulation containing a dose of from 50 mg/kg/Day to 100 mg/kg/Day of coated carnitine granules to a human in need thereof, said carnitine being passed through a 20 mesh screen prior to being coated with at least 39% by weight of a copolymer synthesized from methacrylic acid esters with quaternary ammonium groups, wherein the molar ratio of the ammonium groups to the methacrylic acid esters is 40:1, whereby the release of carnitine is at such a rate that the quantity of carnitine present in the stomach or intestine at any one time is below the amount likely to cause gastrointestinal irritation to the human receiving the carnitine therapy.

2. The method of claim 1, wherein the carnitine granules have a dimension of 25-30 mesh prior to being coated.

3. The method of claim 1, wherein the carnitine in said sustained release formulation is released over a period of time greater than two hours upon exposure to gastrointestinal fluid.

* * * * *